… …

United States Patent [19]

Bargiotti et al.

[11] 4,265,885
[45] May 5, 1981

[54] ANTHRACYCLINES CONTAINING BRANCHED-CHAIN AMINO-DEOXY SUGARS

[75] Inventors: Alberto Bargiotti, Milan; Giuseppe Cassinelli, Pavia; Federico Arcamone; Aurelio DiMarco, both of Milan, all of Italy

[73] Assignee: Farmitalia Carlo Erba S.p.A., Milan, Italy

[21] Appl. No.: 82,293

[22] Filed: Oct. 5, 1979

[30] Foreign Application Priority Data

Oct. 25, 1978 [GB] United Kingdom ............... 41937/78

[51] Int. Cl.³ ..................... C07H 15/24; A61K 31/70
[52] U.S. Cl. ............................... 424/180; 536/17 A; 536/4; 536/53
[58] Field of Search ........................... 536/17 A, 4, 53; 424/180

[56] References Cited

U.S. PATENT DOCUMENTS 4,183,919 1/1980 Cassinelli et al. ................ 536/17 A Primary Examiner—Johnnie R. Brown
Attorney, Agent, or Firm—Hubbell, Cohen, Stiefel & Gross

[57] ABSTRACT

A new class of antitumor glycoside antibiotics of the formula (IA):

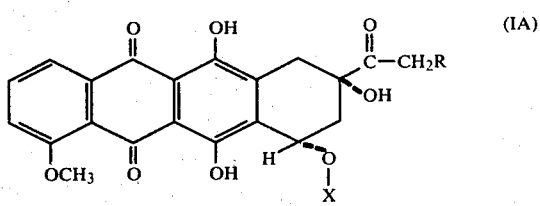

wherein R is hydrogen or hydroxy; and X is

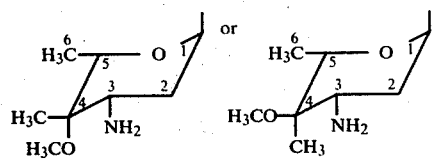

These compounds are prepared, using novel intermediates, by condensing the appropriate aglycone and branched-chain aminodeoxy sugar to form the α-glycosidic linkage.

11 Claims, No Drawings

ANTHRACYCLINES CONTAINING BRANCHED-CHAIN AMINO-DEOXY SUGARS

CROSS-REFERENCE TO RELATED APPLICATIONS

This application is related to, and incorporates by reference the contents of British Patent application No. 53,454, filed Dec. 22, 1976; Belgian Pat. No. 841,266; U.S. Pat. No. 3,803,124 and U.S. Pat. No. 4,039,663, all of them are owned by the unrecorded assignee hereof.

BACKGROUND OF THE INVENTION

1. Field of the Invention

The present invention relates to the antitumor glycosides of the anthracycline type, in particular, certain 4'-C-methyl-4'-O-methyldaunomycin (and adriamycin) derivatives, their preparation, intermediates thereof and their use in antitumor therapy.

2. The Prior Art

The present compounds which are derivatives of daunomycin and adriamycin, both of which are known antitumor antibiotics, are prepared from the aglycone of daunomycin, i.e., daunomycinone, a known compound.

SUMMARY OF THE INVENTION

The invention provides, in one aspect thereof, a new class of antitumor antibiotics of the formula (IA):

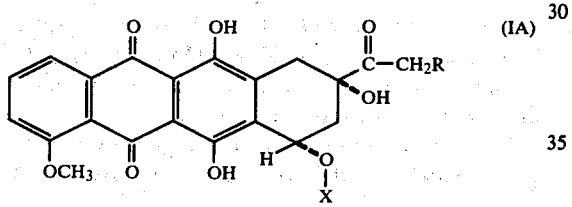

wherein R is hydrogen or hydroxy; and X is

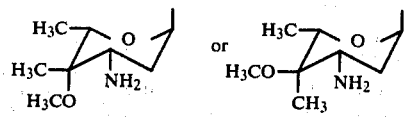

Clearly, when R is hydrogen, these compounds are daunomycin derivatives and when R is hydroxy they are adriamycin derivatives. These new antitumor compounds are: 4'-C-methyl-4'-O-methyldaunomycin, 4'-C-methyl-4'-O-methyladriamycin, 4'-epi-4'-C-methyl-4'-O-methyldaunomycin and 4'-epi-4'-C-methyl-4'-O-methyladriamycin.

The process for making these compounds also comprises part of the invention. According to the process of the invention, a tetracyclic aglycone having a hydroxyanthraquinone chromophoric system of the formula I:

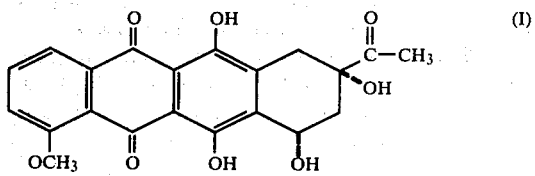

is glycosidically linked to a 3-amino-2,3,6-trideoxy-4-C-methyl-4-O-methyl-L-hexopyranose.

In performing the process, the aglycone of the formula I, which is daunomycinone, is condensed with a protected (N-trifluoroacetyl) 1-halo derivative of a branched-chain aminodeoxy sugar selected from the group consisting of 2,3,6-trideoxy-3-trifluoroacetamido-4-C-methyl-4-O-methyl-L-lyxo-hexopyranosyl chloride (II-E), and 2,3,6-trideoxy-3-trifluoroacetamido-4-C-methyl-4-O-methyl-L-arabino-hexopyranosyl chloride (III-E),

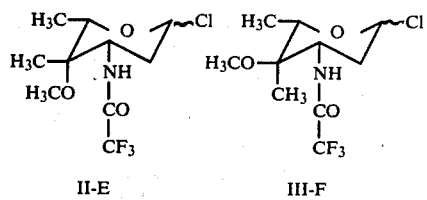

to give respectively, the protected α-glycosides of the formulae IV and VI:

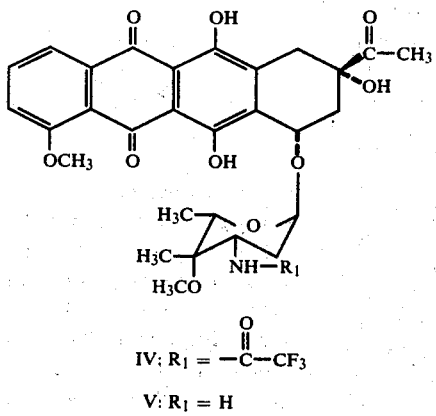

IV: $R_1 = -\overset{O}{\underset{\|}{C}}-CF_3$

V: $R_1 = H$

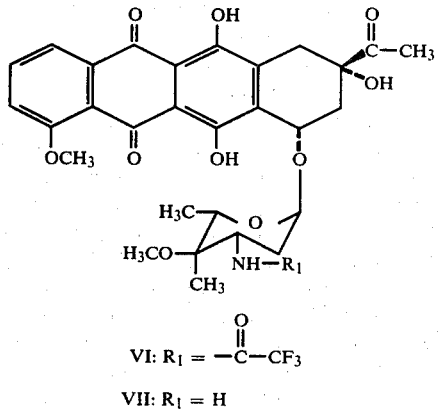

VI: $R_1 = -\overset{O}{\underset{\|}{C}}-CF_3$

VII: $R_1 = H$ from which, after removal of the N-trifluoroacetyl protecting group, the final products V and VII are obtained.

The condensation reaction between the aglycone (I) and the protected halo sugar (II-E or III-E) to form the α-glycosidic linkage is carried out in an inert organic solvent, such as chloroform or methylene dichloride in the presence of a soluble silver salt catalyst, such as silver trifluoromethansulfonate ($AgSO_3CF_3$) and a molecular sieve as a dehydrating agent in accordance with the method described in Belgian Pat. No. 841,266.

The protected halo sugars II-E and III-E are also novel compounds and are thus within the scope of the present invention.

The protected halo sugars II-E and III-E which are reacted with the aglycone (I) are within the scope of this invention and are prepared in the following manner. Methyl-2,3,6-trideoxy-3-trifluoroacetamido-x-L-threo-hexo-pyranosid-4-ulose (X) which is prepared as shown in U.S. Pat. No. 4,039,663 which is herein incorporated by reference, is reacted in accordance with the following equation:

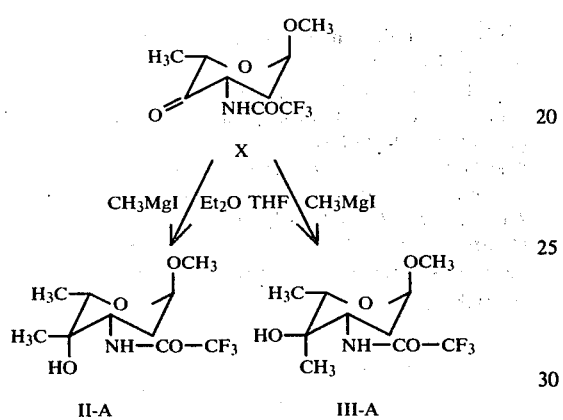

Addition of methylmagnesium iodide to the carbonyl starting compound X is highly stereospecific depending upon the reaction temperature and solvent. Thus, treatment of an ethereal solution of methyl 2,3,6-trideoxy-3-trifluoroacetamido-α-L-threohexo-pyranosid-4-ulose (X) with methylmagnesium iodide at −78° affords methyl 2,3,6-trideoxy-4-C-methyl-3-trifluoroacetamido-α-L-lyxo-hexopyranoside (II-A), whereas addition of methylmagnesium iodide in tetrahydrofuran at reflux gives methyl 2,3,6-trideoxy-4-C-methyl-3-trifluoroacetamido-α-L-arabinohexopyranoside (III-A).

Treatment of the novel intermediates (II-A and III-A) with diazomethane-borontrifluoride etherate reagent in methylene dichloride as described by J. O. Deferrari et al (Methods in Carbohydrate Chemistry, Vol. VI, p. 365, 1972, Academic Pres., New York and London) and in British Patent Application No. 53,454/76 (filed Dec. 22, 1976, both of which are herein incorporated by reference), but at lower temperature (−70°) gives the corresponding previously unknown 4-O-methyl derivatives (II-B and III-B) in good yield.

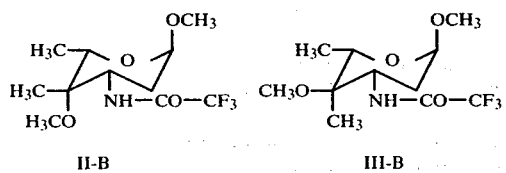

Acid hydrolysis of compounds II-B and III-B, respectively, affords the corresponding compounds II-C and III-C containing a free hydroxyl group in position 1.

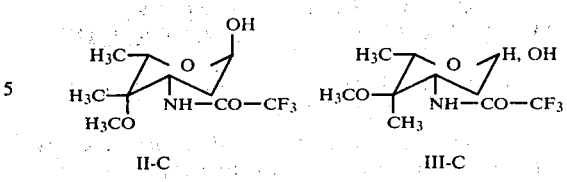

Compounds II-C and III-C, respectively, are reacted with p-nitrobenzoyl chloride in pyridine in order to obtain the corresponding 1-O-p-nitrobenzoyl derivatives II-D and III-D

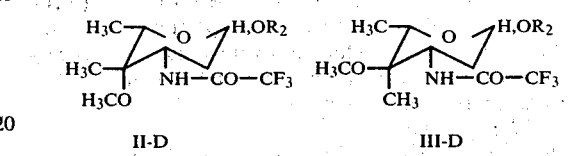

wherein $R_2$ is

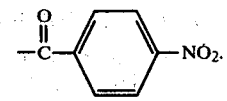

Finally, compounds II-D and III-D are subjected to treatment with dry hydrogen chloride in anhydrous methylene dichloride to give the corresponding 1-chloro derivatives (II-E and III-E).

In order to prepare the compounds of formula (IA), i.e., those wherein R is hydrogen or hydroxy, and X is

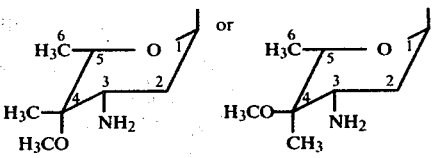

the above-mentioned condensation reaction is effected by using daunomycinone (I) as the aglycone and 2,3,6-trideoxy-4-C-methyl-4-O-methyl-3-trifluoroacetamido-L-lyxo-hexopyranosyl chloride (II-E) or 2,3,6-trideoxy-4-C-methyl-4-O-methyl-3-trifluoroacetamido-L-arabino-hexopyranosyl chloride (III-E) as the protected halo sugar reagent. The coupling reaction affords the protected α-glycosides IV and VI from which, by mild alkaline treatment in order to remove the N-trifluoroacetyl group, 4′-C-methyl-4′-O-methyl-daunomycin (V) and 4′-epi-4′-C-methyl-4′-O-methyl-daunomycin (VII), respectively, are obtained and isolated as the crystalline hydrochlorides.

Subsequent treatment of compounds (V) and (VII) in accordance with the method described in U.S. Pat. No. 3,803,124 (Apr. 9, 1974), which is herein incorporated by reference, leads respectively, to 4′-C-methyl-4′-O-methyl-adriamycin (VIII) and 4′-epi-4′-C-methyl-4′-O-methyl-adriamycin (IX).

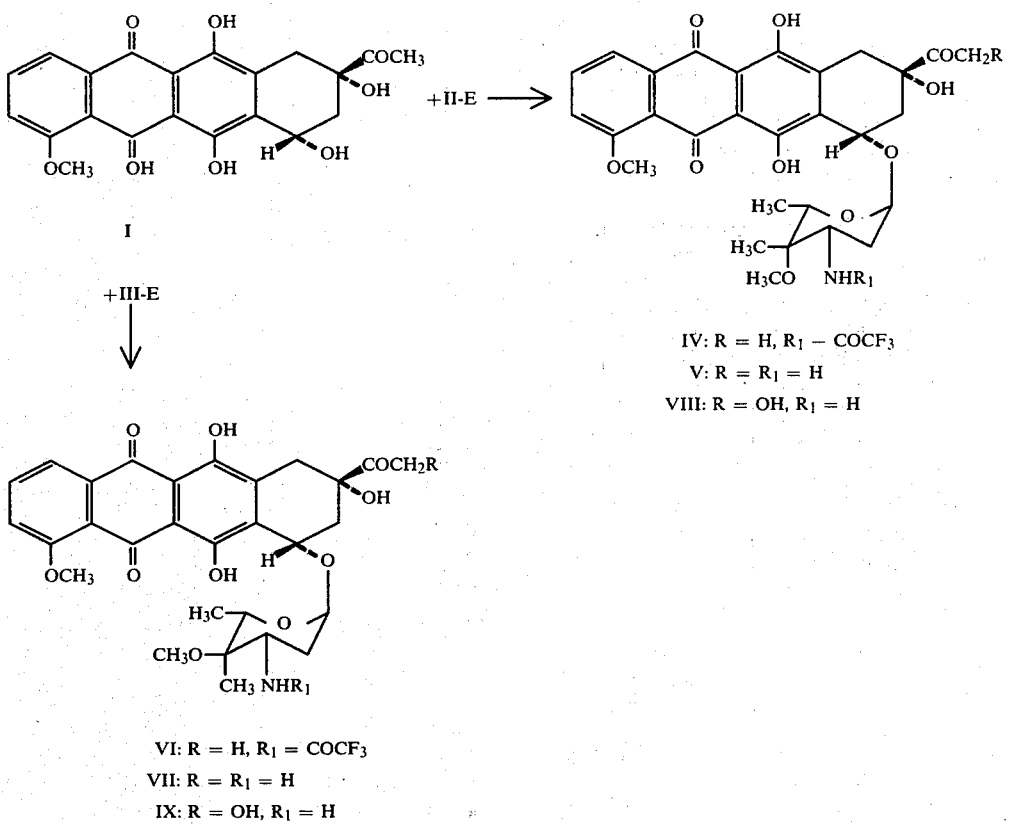

IV: R = H, R₁ — COCF₃
V: R = R₁ = H
VIII: R = OH, R₁ = H

VI: R = H, R₁ = COCF₃
VII: R = R₁ = H
IX: R = OH, R₁ = H

DESCRIPTION OF THE PREFERRED EMBODIMENTS

The invention will now be described in greater detail in conjunction with the following examples (wherein all parts given are by weight unless otherwise specified and degrees of temperature are degrees Celsius).

EXAMPLE 1

Preparation of the intermediate 2,3,6-trideoxy-4-C-methyl-4-O-methyl-3-trifluoroacetamido-L-lyxo-hexopyranosyl chloride An ethereal solution (20 ml) of methyl 2,3,6-trideoxy-3-trifluoroacetamido-4-L-threo-hexopyranosid-4-ulose (X; 1.170 g 4.6 mmoles) prepared as disclosed in U.S. Pat. No. 4,039,663 was added with stirring to an ethereal solution (100 ml) of methylmagnesium iodide (g 2.06 of Mg+7 ml of CH₃J) which was cooled to −78°.

After 3 hours at −78°, water was added, and the ethereal layer was separated. The aqueous layer was extracted with ethyl ether. The combined ethereal extracts were washed with water and dried over anhydrous sodium sulfate.

The residue obtained by evaporation was crystallized from ethyl ether-hexane to give methyl 2,3,6-trideoxy-4-C-methyl-3-trifluoroacetamido-α-L-lyxo-hexopyranoside (II-A, 1.180 g, 95%): m.p. 133°–134°; [α]$_D$ = −128° (c=1 in CHCl₃).

The carbon-13 Nuclear Magnetic Resonance spectrum (DMSOd₆) of compound II-A shows the C-4 methyl group signal at 21.3 p.p.m. (down field from Me₄Si, used as internal reference) a characteristic chemical shift value for equatorial methyl group in branched-chain sugar.

A solution of 1 g (3.7 mmoles) of methyl 2,3,6-trideoxy-4-C-methyl-3-trifluoroacetamido-α-L-lyxo-hexopyranoside (II-A) in 10 ml of dry methylene dichloride was treated at −70° with 0.05 ml of boron trifluoride etherate. While maintaining the temperature at −70°, an excess of diazomethane dissolved in methylene dichloride was added until a faint yellow color persisted. After 60 minutes at −70°, a white solid (polymethylene) was removed by filtration, and the filtrate was washed successively with 10% sodium bicarbonate solution and with water, after which it was dried with anhydrous magnesium sulfate. The residue which was obtained by evaporation was chromatographed on a silica-gel column. Elution with a 95:5 chloroform:acetone mixture gave pure methyl 2,3,6-trideoxy-4-C-methyl-4-O-methyl-3-trifluoroacetamido-α-L-lyxo-hexopyranoside (II-B, 0.68 g, 65%) as a syrup; [α]$_D$ = −129° (c=1.1 in CHCl₃); mass spectrum m/e 285 (M⁺). The pmr spectrum (CDCl₃) showed absorptions at 1.22 (s, CH₃-C-4), 1.28 (d, CH₃-C-5), 3.33 and 3.48 (two s, —OCH₃) and 4.77δ (broad s, C-1-H).

A solution of 0.60 g (2.1 mmoles) of compound II-B in 12 ml. of acetic acid was added to 48 ml of water and heated at 100° for 2 hours. The solution was evaporated to give 2,3,6-trideoxy-4-C-methyl-4-O-methyl-3-trifluoroacetamido-α-L-lyxo-hexopyranose (II-C; 2 g.; 97%) as a syrup; [α]$_D$ = −95° (c=1.1, in CHCl₃). The pmr spectrum (CDCl₃) showed absorptions at: 1.22 (s, CH₃-C-4), 1.26 (d, CH₃-C-5), 3.46 (s, CH₃O) and 5.37δ (broad s, C-1-H).

A solution of 0.50 g (1.85 mmoles) of compound II-C in 12 ml of dry pyridine was treated at 0° with 0.68 g of p-nitro-benzoyl chloride under stirring. After 10 hours at room temperature the reaction mixture was poured into ice-water and the resulting precipitate was filtered off and washed with water to neutrality. The precipitated 1-p-nitrobenzoate (mixture of α and β anomers) was dissolved in chloroform and dried over magnesium sulfate. The residue obtained by evaporation gave 0.735 g of 2,3,6-trideoxy-4-C-methyl-4-O-methyl-1-O-p-nitrobenzoyl-3-trifluoroacetamido-L-lyxo-hexopyranose (II-D, 90%): m.p. 180°–181°; $[\alpha]_D = -42°$ (c=1, in CHCl$_3$).

A solution of 0.70 g (1.66 mmoles) of compound II-D in 15 ml of dry methylene dichloride was saturated at 0° with anhydrous hydrogen chloride. The resulting precipitate of p-nitrobenzoic acid was filtered off under anhydrous conditions and the filtrate was evaporated to a residue which was 2,3,6-trideoxy-4-C-methyl-4-O-methyl-3-trifluoroacetamido-L-lyxo-hexopyranosyl chloride (II-E, 0.45 g). This material was suitable for use in the coupling reaction without further purification.

EXAMPLE 2

Preparation of the intermediate 2,3,6-trideoxy-4-C-methyl-4-O-methyl-3-trifluoroacetamido-L-arabino-hexopyranosyl chloride (III-E)

Methyl 2,3,6-trideoxy-3-trifluoroacetamido-α-L-threo-hexopyranosid-4-ulose prepared in accordance with U.S. Pat. No. 4,039,663 (X, 1.76 g, 6.9 mmoles) in dry tetrahydrofuran (35 ml) was added to a refluxing solution of methylmagnesiumiodide (g 3.1 of Mg+10.5 ml of CH$_3$J) in dry tetrahydrofuran (150 ml).

After refluxing for 3 hours the reaction mixture was diluted with chloroform and water, the phases were separated and the aqueous layer was then extracted with chloroform.

The combined chloroform extracts were washed with water and dried over anhydrous sodium sulfate.

The residue (1.85 g) obtained by evaporation was chromatographed on a silica gel column.

The elution with a 97:3 chloroform:acetone mixture afforded two compounds. The minor compound was identified as methyl 2,3,6-trideoxy-4-C-methyl-3-trifluoroacetamido-α-L-lyxo-hexopyranoside (II-A, 0.280 g, 15%), whereas the major compound was crystallized from isopropyl ether and identified as methyl 2,3,6-trideoxy-4-C-methyl-3-trifluoroacetamido-α-L-arabinohexopyranoside (III-A, 1.40 g, 75%): m.p. 140°–141°, $[\alpha]_D^{23°} = -155°$ (c=1.1, in CHCl$_3$); mass spectrum m/e 271 (M+). The carbon-13 Nuclear Magnetic Resonance spectrum (DMSO d$_6$) of compound III-A shows the C-4 methyl group signal at 13.6 p.p.m. (down field from Me$_4$Si, used as internal reference) a characteristic chemical shift value for axial methyl group in branched-chain sugar.

Treatment of methyl-2,3,6-trideoxy-4-C-methyl-3-trifluoroacetamido-α-L-arabino-hexopyranoside (III-A, 1.30 g, 4.8 mmoles) in methylene dichloride (10 ml) with diazomethane/boron-trifluoride, as described in Example 1 gave the corresponding 4-O-methylderivative (III-B, 1.03 g, 75%) as a syrup: $[\alpha]_D^{23°} = -118°$ (c=1, in CHCl$_3$); mass spectrum m/e 285 (M+); pmr spectrum (CDCl$_3$): 1.12 (s, CH$_3$-C-4), 1.17 (d, CH$_3$-C-5), 3.22 and 3.33 (two s, OCH$_3$) and 4.66δ (m, C-1-H). Acid hydrolysis of compound III-B as in Example 1 (1 g, 3.5 mmoles) gave 2,3,6-trideoxy-4-C-methyl-4-O-methyl-3-trifluoroacetamido-L-arabino-hexopyranose (III-C, 0.94 g, 95%) as a syrup: $[\alpha]_D^{23°} = -70°$ (c=1, in CHCl$_3$); pmr spectrum (CDCl$_3$): 1.12 (s, CH$_3$-C-4), 1.16 (d, CH$_3$-C-5), 3.24 (s, OCH$_3$) and 5.28δ (broad s, C-1-H).

Treatment of compound III-C (0.90 g, 3.3 mmoles) with p-nitro-benzoyl chloride in pyridine as described in Example 1 gave the corresponding 1-O-p-nitrobenzoyl derivative (III-D, 1.26 g., 90%): m.p. 175°–176°; $[\alpha]_D^{23°} = -40°$ (c=1.1, in CHCl$_3$).

A solution of compound III-D (1 g, 2.4 mmoles) in dry methylene dichloride was saturated at 0° with anhydrous hydrogen chloride. After filtration of the precipitated p-nitrobenzoic acid, the solution was evaporated to dryness to give the resulting 2,3,6-trideoxy-4-C-methyl-4-O-methyl-trifluoroacetamido-L-arabino-hexopyranosyl chloride (III-E, 0.65 g).

EXAMPLE 3

4'-C-Methyl-4'-O-methyl-daunomycin (IMI 96)

To a solution of daunomycinone (0.816 g, 2.05 mmoles) in dry methylene dichloride (80 ml) was added 2,3,6-trideoxy-4-C-methyl-4-O-methyl-3-trifluoroacetamido-L-lyxo-hexopyranosyl chloride (II-E, 0.45 g in 10 ml of methylene dichloride), and molecular sieve (4 Å Merck, 5 g). The mixture was treated with 0.40 g of AgSO$_3$CF$_3$ in anhydrous ethylether (10 ml) under vigorous stirring. After 1 hour at room temperature, the reaction mixture was neutralized with a saturated aqueous solution of NaHCO$_3$, and the organic phase was separated and evaporated under vacuum. Chromatographic purification of the crude residue on a column of silicic acid, using 95:5 chloroform:acetone as the eluent, gave 0.72 g of 4'-C-methyl-4'-O-methyl-N-trifluoroacetyldaunomycin (IV): m.p. 91°–93°; $[\alpha]_D^{23°} = +222°$ (c=0.05, in CHCl$_3$). The pmr spectrum (CDCl$_3$) showed absorption at 1.19 (s, CH$_3$-C-4'), 1.32 (d, CH$_3$-C-5'), 2.39 (s, CH$_3$-CO), 3.45 (s, C-4'-O-CH$_3$), 4.04 (s, C-4-O-CH$_3$), 5.25 (broad s, C-7-H), 5.47 (broad s, C-1'-H), 13.17 and 13.86δ (two s, phenolic OH).

A solution of 0.6 g of compound IV in 10 ml of acetone was treated with 45 ml of 0.2 N aqueous sodium hydroxide and stirred under nitrogen at room temperature. After 2 hours the reaction mixture was adjusted to pH 3.5 with 1 N aqueous hydrogen chloride and then extracted with chloroform to eliminate impurities. The aqueous phase, adjusted to pH 8.2, was extracted twice with chloroform (50 and 30 ml portions). The combined organic extracts were dried over Na$_2$SO$_4$, concentrated to a small volume and acidified to pH 4.5 with 0.5 N methanolic hydrogen chloride. An excess of diethyl ether was added to yield 4'-C-methyl-4'-O-methyl-daunomycin (V) as the hydrochloride (0.38 g, 68%): m.p. 178°–180° (dec.); $[\alpha]_D = +285°$ (c=0.05 in CH$_3$OH).

EXAMPLE 4

4'-C-Methyl-4'-O-methyl-adriamycin (VIII) (IMI 97)

A solution of 4'-C-methyl-4'-O-methyl-daunomycin hydrochloride (0.3 g, 0.5 mmoles) in a mixture of 4 ml of anhydrous methanol, 11.5 ml of dioxane and 0.30 ml of ethyl orthoformate was treated with 1.2 ml of a solution containing 0.93 g of bromine in 10 ml of chloroform. After 2 hours at 10°, the reaction mixture was poured into a mixture of 60 ml of ethyl ether and 30 ml of petroleum ether. The resulting red precipitate was filtered and washed with ethyl ether several times to completely remove the acidity and then was dissolved in a mixture of 10 ml of acetone and 10 ml of 0.25 N aqueous hydrogen bromide. After 20 hours at 30° the reaction mixture was treated with 0.45 g of sodium formate in 5 ml of water and stirred at 30° for 48 hours. The resulting mixture was extracted with chloroform in order to remove some lipophilic impurities. The aqueous phase, after being adjusted to pH 7.6 with aqueous NaHCO$_3$, was repeatedly extracted with chloroform until the extracts were colorless. The combined chloroform extracts were dried with Na$_2$SO$_4$ and evaporated to a small volume (about 15 ml) under vacuum. The resulting red solution was adjusted to pH 3.5 with anhydrous methanolic hydrogen chloride, an excess of ethyl ether was added to give 4'-C-methyl-4'-O-methyl-adriamycin (VIII, 0.21 g) as the hydrochloride: m.p. 185°–186° (dec.); $[\alpha]_D^{23°} = +291°$ (c=0.05, in CH$_3$OH).

EXAMPLE 5

4'-Epi-4'-C-methyl-4'-O-methyl-daunomycin (VII) (IMI 98)

The synthesis of the compound VII, starting from daunomycinone (I) and 2,3,6-trideoxy-4-C-methyl-4-O-methyl-3-trifluoroacetamido-L-arabino-hexopyranosyl chloride (III-E) was performed according to the procedure described in Example 3.

4'-Epi-4'-C-methyl-4'-O-methyl-daunomycin (VII) was obtained as the hydrochloride in the form of red crystals: m.p. 187°–188° (dec.); $[\alpha]_D^{23°} = +251°$ (c=0.05, in CH$_3$OH).

EXAMPLE 6

4'-Epi-4'-C-methyl-4'-O-methyl-adriamycin (IX) (IMI 101)

The 14-bromo-derivative of compound VII was obtained and successively hydroxylated at the 14-position according to the procedure described in Example 4. By this procedure, 4'-epi-4'-C-methyl-4'-O-methyl-adriamycin (IX) was obtained as the hydrochloride in the form of red crystals: m.p. 190°–191° C. (dec.); $[\alpha]_D^{23°} = +272°$ (c=0.025, in CH$_3$OH).

BIOLOGICAL ACTIVITY

The new anthracycline glycosides described in the invention, display antitumor activity. The compounds have been tested against HeLa cells "in vitro" (time of exposure to the drugs: 24 hours) and on P 388 leukemia in mice in comparison with daunorubicin and doxorubicin. The results of the "in vitro" tests, shown in Table I are reported as ID$_{50}$ (Inhibiting Dose 50% in ng/ml).

It can be observed that all the compounds inhibited the cell viability of HeLa cells in vitro.

The antitumor activity was tested "in vivo" on P 388 leukemia in comparison with daunorubicin and doxorubicin.

The data reported in Table II show that all the new anthracycline glycosides display antitumor activity at non-toxic doses.

TABLE I

| Activity on HeLa cells viability in vitro | |
|---|---|
| Compound[a] | ID$_{50}$ ng/ml |
| Daunorubicin | 10 |
| 4'-C-methyl-4'-O-methyl-daunorubicin (V) | 34 |
| 4'-epi-4'-C-methyl-4'-O-methyl-daunorubicin (VII) | 2.5–3.4 |
| Doxorubicin | 10 |
| 4'-C-methyl-4'-O-methyl-doxorubicin (VIII) | 5 |

TABLE I-continued

| Activity on HeLa cells viability in vitro | |
|---|---|
| Compound[a] | ID$_{50}$ ng/ml |
| 4'-epi-4'-C-methyl-4'-O-methyl-doxorubicin (IX) | 27 |

[a]As hydrochloride

TABLE II

| Activity against P 388 leukemia | | | |
|---|---|---|---|
| Compound[c] | Dose[a] mg/kg | T/C[b] % | No. of toxic deaths/total |
| Daunorubicin | 2.9 | 163 | 0/48 |
| | 4.4 | 161 | 3/48 |
| | 6.6 | 156 | 28/48 |
| 4'-C-methyl-4'-O-methyl-daunorubicin (V) | 6.6 | 140 | 0/18 |
| | 22.5 | 155 | 0/20 |
| | 33.7 | 150 | 0/26 |
| | 50.5 | 137 | 1/5 |
| 4'-epi-4'-C-methyl-4'-O-methyl-daunorubicin (VII) | 6.6 | 140 | 0/8 |
| | 10.0 | 147 | 0/8 |
| | 22.5 | 150 | 0/8 |
| Doxorubicin | 4.4 | 190 | 0/28 |
| | 6.6 | 201 | 0/28 |
| | 10.0 | 241 | 5/28 |
| 4'-C-methyl-4'-O-methyl-doxorubicin (VIII) | 4.4 | 165 | 0/10 |
| | 6.6 | 172 | 0/10 |
| | 10.0 | 202 | 2/17 |
| 4'-epi-4'-C-methyl-4'-O-methyl-doxorubicin (IX) | 4.4 | 165 | 0/8 |
| | 6.6 | 185 | 0/8 |
| | 10.0 | 205 | 0/8 |

[a]Mice were treated i.p. on day 1 after tumor cell inoculation.
[b]Median survival time of treated mice, over median survival time of control × 100.
[c]As hydrochloride.

Variations and modifications can, of course, be made without departing from the spirit and scope of the invention.

Having thus described our invention, what we desire to secure by Letters Patent and hereby claim is:

1. A compound of general formula I:

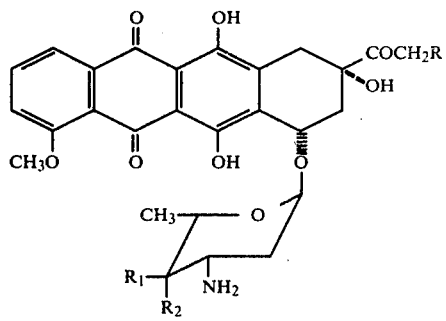

in which R represents a hydrogen atom or a hydroxy group, one of R$_1$ and R$_2$ represents a methyl group and the other of R$_1$ and R$_2$ represents a methoxy group.

2. 4'-C-methyl-4'-O-methyl-daunorubicin hydrochloride.

3. 4'-epi-4'-C-methyl-4'-O-methyl-daunorubicin hydrochloride.

4. 4'-C-methyl-4'-O-methyl-doxorubicin hydrochloride.

5. 4'-epi-4'-C-methyl-4'-O-methyl-doxorubicin hydrochloride.

6. A pharmaceutical composition containing a therapeutically effective amount of an anthracycline glycoside of general formula I according to any of claims 1 to 5 in combination with a therapeutically acceptable diluent or carrier.

7. A compound of the formula:

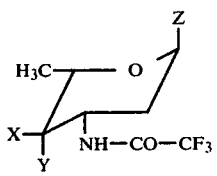

where X is H₃C when Y is H₃CO or OH and X is H₃CO or OH when Y is H₃C;

where Z is OCH₃; H, OR; H; Cl; or OH;

where R is

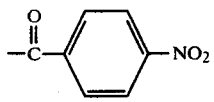

8. The hydrochloride of the compounds of claim 7.

9. 2,3,6-Trideoxy-4-C-methyl-4-O-methyl-3-trifluoroacetamido-L-lyxo-hexopyranosyl chloride.

10. 2,3,6-Trideoxy-4-C-methyl-4-O-methyl-3-trifluoroacetamido-L-arabino-hexopyranosyl chloride.

11. A method for treating leukemia $P_{388}$ in a host comprising treating the host with a therapeutically effective amount of a compound selected from the group consisting of 4'-C-methyl-4'-O-methyl-daunorubicin, 4'-epi-4'-C-methyl-4'-O-methyl-daunorubicin hydrochloride; 4-C-methyl-4'-O-methyl-doxorubicin hydrochloride and 4'-epi-4'-C-methyl-4'-O-methyl-doxorubicin hydrochloride.

* * * * *

UNITED STATES PATENT AND TRADEMARK OFFICE
CERTIFICATE OF CORRECTION

PATENT NO. : 4,265,885

DATED : May 5, 1981

INVENTOR(S) : Alberto Bargiotti, et al

It is certified that error appears in the above—identified patent and that said Letters Patent is hereby corrected as shown below:

Column 5, line 48: "-4-L" should read -- -α-L --.

Signed and Sealed this

Sixth Day of October 1981

[SEAL]

Attest:

GERALD J. MOSSINGHOFF

Attesting Officer   Commissioner of Patents and Trademarks